(12) United States Patent
Micklem

(10) Patent No.: US 9,801,880 B2
(45) Date of Patent: Oct. 31, 2017

(54) USE OF KINASE INHIBITORS

(71) Applicant: BerGenBio AS, Bergen (NO)

(72) Inventor: David Robert Micklem, Bergen (NO)

(73) Assignee: BerGenBio AS, Bergen (NO)

( * ) Notice: Subject to any disclaimer, the term of this patent is extended or adjusted under 35 U.S.C. 154(b) by 0 days.

(21) Appl. No.: 15/100,891

(22) PCT Filed: Nov. 28, 2014

(86) PCT No.: PCT/GB2014/053548
§ 371 (c)(1),
(2) Date: Jun. 1, 2016

(87) PCT Pub. No.: WO2015/082887
PCT Pub. Date: Jun. 11, 2015

(65) Prior Publication Data
US 2016/0339021 A1    Nov. 24, 2016

(30) Foreign Application Priority Data

Dec. 2, 2013 (GB) .................................. 1321227.9
Dec. 24, 2013 (GB) .................................. 1323021.4

(51) Int. Cl.
A61K 31/502 (2006.01)
A61K 31/4196 (2006.01)

(52) U.S. Cl.
CPC ........ A61K 31/502 (2013.01); A61K 31/4196 (2013.01)

(58) Field of Classification Search
CPC .......................... A61K 31/4196; A61K 31/502
See application file for complete search history.

(56) References Cited

U.S. PATENT DOCUMENTS

2011/0028473 A1  2/2011  Adibhatla Kali Satya et al.
2012/0171670 A1  7/2012  Ma

FOREIGN PATENT DOCUMENTS

WO   20050049032 A1   6/2005
WO   2008083367 A2    7/2008
WO   2010083465 A1    7/2010

OTHER PUBLICATIONS

Anderson (Chem and Biol 10:787-797, 2003.*
(Continued)

Primary Examiner — Savitha Rao
(74) Attorney, Agent, or Firm — Stites & Harbison, PLLC; Mandy Wilson Decker; Sean Ritchie

(57) ABSTRACT

The invention provides a compound for use for treating, preventing or managing a condition associated with the activation, mutation and/or over-expression of one or more kinases, wherein if the condition is associated with Axl over-expression, it is also associated with the activation, mutation and/or over-expression of one or more other kinases, and wherein the compound has a structure according to formula (I) : wherein the symbols used in formula (I) are as defined herein.

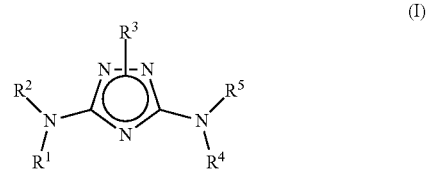

8 Claims, 7 Drawing Sheets

A

B

(56) References Cited

OTHER PUBLICATIONS

Figure 1:
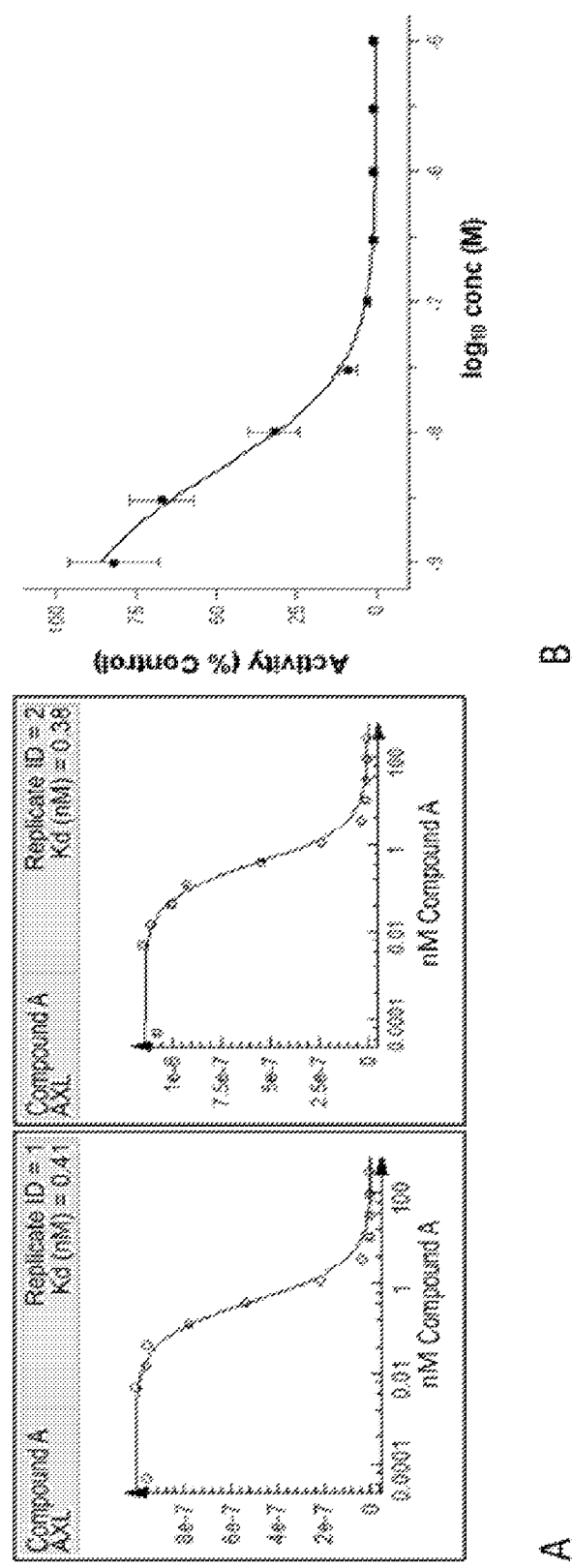

Thiel (Nature Biotechnol 2:513-519, 2004).*
European Patent Office, International Search Report issued in corresponding Application No. PCT/GB2014/053548, dated Jun. 5, 2015.
Erdmann, et al. "Axl Represents a Therapeutic Target in T315I-Mutated and WT Chronic Myeloid Leukemia," Blood (2013) vol. 122 (21), p. 1469.
Schultze, et al. "Prognostic Significance and Target Potential of Axl in Acute Myeloid Leukemia," Blood (2011) vol. 118 (21), p. 421.
Holland, et al. "R428, a Selective Small Molecule Inhibitor of Axl Kinase, Blocks Tumor Spread and Prolongs Survival in Models of Metastatic Breast Cancer," Cancer Research, American Association for Cancer Research (2010) vol. 70 (4), p. 1544-1554.
Verma, et al. "Targeting Axl and Mer Kinases in Cancer," Molecular Cancer Therapeutics (2011) vol. 10 (10), p. 1763-1773.

* cited by examiner

SEQUENCE LISTING

```
<160> NUMBER OF SEQ ID NOS: 4

<210> SEQ ID NO 1
<211> LENGTH: 22
<212> TYPE: DNA
<213> ORGANISM: Homo sapiens

<400> SEQUENCE: 1
gaagcttctc cctgacatcc gt                                              22

<210> SEQ ID NO 2
<211> LENGTH: 22
<212> TYPE: DNA
<213> ORGANISM: Homo sapiens

<400> SEQUENCE: 2
gccaggctct cgggtgcagt cc                                              22

<210> SEQ ID NO 3
<211> LENGTH: 24
<212> TYPE: DNA
<213> ORGANISM: Homo sapiens

<400> SEQUENCE: 3
gcgcaacaag cccactgtct atgg                                            24

<210> SEQ ID NO 4
<211> LENGTH: 22
<212> TYPE: DNA
<213> ORGANISM: Homo sapiens

<400> SEQUENCE: 4
gccaggctct cgggtgcagt cc                                              22
```

USE OF KINASE INHIBITORS

This invention relates to the use of a group of compounds that are receptor protein tyrosine kinase inhibitors. In particular, it relates to the use of such compounds in the treatment or prevention of one or more conditions in which the functional effects of one or more kinases are elevated.

All of the protein kinases that have been identified to date in the human genome share a highly conserved catalytic domain of around 300 amino acids. This domain folds into a bi-lobed structure in which reside ATP-binding and catalytic sites. The complexity of protein kinase regulation allows many potential mechanisms of inhibition including competition with activating ligands, modulation of positive and negative regulators, interference with protein dimerization, and allosteric or competitive inhibition at the substrate or ATP binding sites.

Axl (also known as UFO, ARK, and Tyro7; nucleotide accession numbers NM_021913 and NM_001699; protein accession numbers NP_068713 and NP_001690) is a receptor protein tyrosine kinase (RTK) that comprises a N-terminal extracellular ligand-binding domain and C-terminal cytoplasmic region containing the catalytic domain. Axl and its two close relatives, MerTK/Nyk and Sky (Tyro3/Rse/Dtk), collectively known as the TAM family of RTK's, all bind and are stimulated to varying degrees by the same ligand, Gas6 (growth arrest specific-6), a ~76 kDa secreted protein with significant homology to the coagulation cascade regulator, Protein S. In addition to binding to ligands, the Axl extracellular domain has been shown to undergo homophilic interactions that mediate cell aggregation, suggesting that one important function of Axl may be to mediate cell-cell adhesion.

In WO2008/083367, a group of compounds are disclosed as inhibitors of Axl. Such inhibition is shown to lead to antineoplastic effects. No suggestion is made, however, that the Axl-inhibiting compounds may have effects on other kinases.

In accordance with a first aspect of the invention, there is provided a compound for use for treating, preventing or managing a condition associated with the activation, mutation and/or over-expression of one or more kinases, wherein if the condition is associated with Axl over-expression, it is also associated with the activation, mutation and/or over-expression of one or more other kinases, and wherein the compound has a structure according to formula (I):

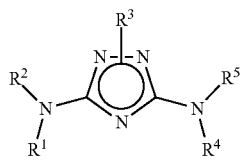

(I)

wherein:
R$^1$, R$^4$ and R$^5$ are each independently selected from the group consisting of hydrogen, alkyl, alkenyl, aryl, aralkyl, —C(O)R$^8$, —C(O)N(R$^6$)R$^7$, and —C(=NR$^6$)N(R$^6$)R$^7$;

R$^2$ and R$^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OR$^8$, —R$^9$—O—R$^{10}$—OR$^8$, —R$^9$—O—R$^{10}$—OR$^8$, —R$^9$—O—R$^{10}$—CN, —R$^9$—O—R$^{10}$—C(O)OR$^8$, —R$^9$—O—R$^{10}$—C(O)N(R$^6$)R$^7$, —R$^9$—O—R$^{10}$—S(O)$_p$R$^8$ (where p is 0, 1 or 2), —R$^9$—O—R$^{10}$—N(R$^6$)R$^7$, —R$^9$—O—R$^{10}$—C(NR$^{11}$)N(R$^{11}$)H, —R$^9$—OC(O)—R$^8$, —R$^9$—N(R$^6$)R$^7$, —R$^9$—C(O)R$^8$, —R$^9$—C(O)OR$^8$, —R$^9$—C(O)N(R$^6$)R$^7$, —R$^9$—N(R$^6$)C(O)OR$^8$, —R$^9$—N(R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^9$—S(O)$_t$N(R$^6$)R$^7$ (where t is 1 or 2);

or R$^2$ is a polycyclic heteroaryl containing more than 14 ring atoms as described above and R$^3$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{13}$—OR$^{12}$, —R$^{13}$—OC(O)—R$^{12}$, —R$^{13}$—O—R$^{14}$—N(R$^{12}$)$_2$, —R$^{13}$—N(R$^{12}$)—R$^{14}$—N(R$^{12}$)$_2$, —R$^{13}$—N(R$^{12}$)—R$^{14}$—N(R$^{12}$)$_2$, —R$^{13}$—N(R$^{12}$)$_2$, —R$^{13}$—C(O)R$^{12}$, —R$^{13}$—C(O)OR$^{12}$, —R$^{13}$—C(O)N(R$^{12}$)$_2$, —R$^{13}$—C(O)N(R$^{12}$)—R$^{14}$—N(R$^{12}$)R$^{13}$, —R$^{13}$—C(O)N(R$^{12}$)—R$^{14}$—OR$^{12}$, —R$^{13}$—N(R$^{12}$)C(O)OR$^{12}$, —R$^{13}$—N(R$^{12}$)C(O)R$^{12}$, —R$^{13}$—N(R$^{12}$)S(O)$_t$R$^{12}$ (where t is 1 or 2), —R$^{13}$—S(O)$_t$OR$^{12}$ (where t is 1 or 2), —R$^{13}$—S(O)$_p$R$^{12}$ (where p is 0, 1 or 2), and —R$^{13}$—S(O)$_t$N(R$^{12}$)$_2$ (where t is 1 or 2);

or R$^3$ is a polycyclic heteroaryl containing more than 14 ring atoms as described above, and R$^2$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{13}$—OR$^{12}$, —R$^{13}$—OC(O)—R$^{12}$, —R$^{13}$—O—R$^{14}$—N(R$^{12}$)$_2$, —R$^{13}$—N(R$^{12}$)—R$^{14}$—N(R$^{12}$)$_2$, —R$^{13}$—N(R$^{12}$)—R$^{14}$—N(R$^{12}$)$_2$, —R$^{13}$—N(R$^{12}$)$_2$, —R$^{13}$—C(O)R$^{12}$, —R$^{13}$—C(O)OR$^{12}$, —R$^{13}$—C(O)N(R$^{12}$)$_2$, —R$^{13}$—C(O)N(R$^{12}$)—R$^{14}$—N(R$^{12}$)R$^{13}$, —R$^{13}$—C(O)N(R$^{12}$)—R$^{14}$—OR$^{12}$, —R$^{13}$—N(R$^{12}$)C(O)OR$^{12}$, —R$^{13}$—N(R$^{12}$)C(O)R$^{12}$, —R$^{13}$—N(R$^{12}$)S(O)$_t$R$^{12}$ (where t is 1 or 2), —R$^{13}$—S(O)$_t$OR$^{12}$ (where t is 1 or 2), —R$^{13}$—S(O)$_p$R$^{12}$ (where p is 0, 1 or 2), and —R$^{13}$—S(O)$_t$N(R$^{12}$)$_2$ (where t is 1 or 2);

each R$^6$ and R$^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{10}$—OR$^8$, —R$^{10}$—CN, —R$^{10}$—NO$_2$, —R$_{10}$—N(R$^8$)$_2$, —R$^{10}$—C(O)OR$^8$ and —R$^{10}$—C(O)N(R$^8$)$_2$, or any R$^6$ and R$^7$, together with the common nitrogen to which they are both attached, form an optionally substituted N-heteroaryl or an optionally substituted N-heterocyclyl;

each R$^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each R$^9$ is independently selected from the group consisting of a direct bond, an optionally substituted straight or branched alkylene chain, an optionally substituted straight or branched alkenylene chain and an optionally substituted straight or branched alkynylene chain;

each R$^{10}$ is independently selected from the group consisting of an optionally substituted straight or branched alkylene chain, an optionally substituted straight or branched alkenylene chain and an optionally substituted straight or branched alkynylene chain;

each R$^{11}$ is independently selected from the group consisting of hydrogen, alkyl, cyano, nitro and —OR$^8$;

each R$^{12}$ is independently selected from the group consisting of hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl, optionally substituted heteroarylalkyl, —R$^{10}$—OR$^8$, —R$^{10}$—CN, —R$^{10}$—NO$_2$, —R$^{10}$—N(R$^8$)$_2$, —R$^{10}$—C(O)OR$^8$ and —R$^{10}$—C(O)N(R$^8$)$_2$, or two R$^{12}$'s, together with the common nitrogen to which they are both attached, form an optionally substituted N-heterocyclyl or an optionally substituted N-heteroaryl;

each R$^{13}$ is independently selected from the group consisting of a direct bond, an optionally substituted straight or branched alkylene chain and an optionally substituted straight or branched alkenylene chain; and each R$^{14}$ is independently selected from the group consisting of an optionally substituted straight or branched alkylene chain and an optionally substituted straight or branched alkenylene chain;

an isolated stereoisomer or mixture thereof, or a tautomer or mixture thereof, or a pharmaceutically acceptable salt or N-oxide thereof.

Compounds of formula (I) are disclosed in WO2008/083367. The contents of this document, in particular the synthesis and characterisation details for the compounds of formula (I), are incorporated herein by reference in their entirety.

It has been found that compounds of formula (I) are capable of inhibiting a number of kinases in addition to Axl. This surprising finding opens up a number of new uses for the compounds. The condition to be treated, managed or prevented may or may not be associated with Axl over-expression. According to the invention, if the condition to be treated is associated with over-expression of Axl, it is also associated with activation, mutation and/or over-expression of one or more other kinases. In such conditions, this dual (or multiple) kinase inhibition may lead to an enhanced activity of the compounds against the condition. In conditions in which Axl over-expression does not feature, inhibition of the one or more other kinases nevertheless has the potential to lead to prevention or attenuation of the disease state.

Compounds that are able to inhibit multiple kinases have the potential to provide more effective treatments of a variety of conditions. Such compounds may be able to modulate multiple pathways within cells, and in particular may be used to target cells that have developed resistance to inhibitors of one of the kinases.

In an embodiment, the condition to be treated, managed or prevented is not associated with Axl over-expression.

In particular embodiments, the condition is a neoplastic condition, such as cancer or a pre-cancerous neoplasia. In an embodiment, the condition may be acute lymphoblastic leukemia, multiple myeloma, clear cell renal cell carcinoma, myelodysplastic syndromes, medullary thyroid carcinoma, gastrointestinal stromal tumours, pheochromocytoma, myeloid leukemia, including chronic myeloid leukemia or acute myeloid leukemia, melanoma, non-small cell lung carcinoma or lymphoma. For example, the condition may be acute lymphoblastic leukemia, multiple myeloma, clear cell renal cell carcinoma, myelodysplastic syndromes, medullary thyroid carcinoma, gastrointestinal stromal tumours, or pheochromocytoma. In particular, the condition may be gastrointestinal stromal tumours, or pheochromocytoma. In an embodiment, the condition may be myeloid leukemia.

Non-neoplastic conditions which may be treated, managed or prevented according to the invention include inflammatory conditions (e.g. rheumatoid arthritis), endometriosis, vascular disease/injury (including but not limited to restenosis, atherosclerosis and thrombosis), psoriasis, visual impairment due to macular degeneration, diabetic retinopathy and retinopathy of prematurity, kidney disease (including but not limited to glomerulonephritis, diabetic nephropathy and renal transplant rejection), pulmonary disorders (such as COPD), osteoporosis, osteoarthritis, viral infection, fibrosis (such as liver fibrosis) and cataracts.

The condition to be treated may, in certain embodiments, be associated with the activation, mutation and/or over-expression of one or more kinases selected from those which are encoded by the genes MERTK (ENSG00000153208), TEK (ENSG00000120156), YES1 (ENSG00000176105), FLT1 (ENSG00000102755), FLT3 (ENSG00000122025), FLT4 (ENSG00000037280), BMX (ENSG00000102010), ABL1 (ENS G00000097007), RET (ENS G00000165731), KIT (ENSG00000157404), YSK4 (ENSG00000176601), SLK (ENSG00000065613), WEE1 (ENSG00000166483), WEE2 (ENSG00000214102), MAP3K2 (ENSG00000169967), MAP4K1 (ENSG00000104814), STK10 (ENSG00000072786), and LCK (ENSG00000182866).

The compounds of formula (I) have been found to have inhibitory activity at all the kinases identified above. The gene identification numbers given herein refer to the Ensembl database (www.ensembl.org). Splice variants of these kinases are also intended to be covered by this listing.

Where reference is made to Abl (or the corresponding gene, ABL) herein, this should be understood to mean the kinase (or corresponding gene) Abl1 (ABL1). Moreover, mutant Abl1 is intended to include the Bcr-Abl1 (BCR-ABL1) fusion protein (gene), i.e. that which is present in Philadelphia chromosome. In addition, references to this mutant kinase also include those of the 'doubly' mutant type, i.e. in which the Bcr-Abl1 (BCR-ABL1) fusion protein (gene) itself contains a further mutation, e.g. such as T135I, which can for example lead to resistance to existing kinase inhibitors (such as imatinib).

In embodiments of the present invention, the condition is associated with one or more mutant kinases. Particular mutant kinases of relevance include those which are encoded by the genes: ABL1(T315I), ABL1(Q252H), ABL1 (H396P), ABL1(Y253F), ABL1(M351T), ABL1(E255K), KIT(A829P), KIT(D816H), KIT(V560G), KIT(D816V), KIT(V654A), FLT3(D835Y), FLT3(D835H), FLT3 (K663Q), FLT3(N841I), RET(V804L), RET(V804M), RET (M918T), TEK(Y897S), and TEK(R849W).

In the nomenclature used herein to define mutant kinases, the letters before the parentheses indicate the kinase concerned, the first letter inside the parentheses denotes the amino acid residue (using the standard one-letter abbreviation system for amino acids) of the wild-type kinase which is present at the position indicated by the number in the parentheses, and the letter to the right of the number indicates the amino acid residue which is present at that position in the mutant kinase. Thus ABL1(T315I) denotes the ABL1 mutant kinase in which the threonine present at position 315 in wild-type ABL1 is replaced by isoleucine. The mutant kinases defined herein are the expression products of allelic variants of the wild-type genes, in which alleles the genetic coding is changed in such a way that the defined amino acid substitution is present in the protein product.

As would be appreciated by the skilled person, kinases are sometimes referred to by multiple names, even though the same kinase protein (or gene) is concerned. The NCBI Gene database (http://www.ncbi.nlm.nih.gov/gene) provides links between the different names for particular kinases.

It has been determined that, in several instances, the compounds of formula (I) show an enhanced inhibitory activity at mutant kinases compared to the corresponding wild-type kinases. When the compounds of formula (I) are used in a condition associated with the mutation of one or more kinases, this property provides a potential improvement in selectivity of the compounds for cells expressing the mutant kinase(s). For example, where the compounds are used in a neoplastic condition involving mutant kinase(s), the effects of the compounds on cell signaling, growth and/or division will be enhanced in cells associated with the neoplasia, and correspondingly reduced in non-neoplastic cells. This should result in a reduction of side-effects, and an improvement in the therapeutic window.

According to the present invention, the compound of formula I may be used in sequential or simultaneous combination with one or more additional active pharmaceutical ingredients. Such additional active ingredients may be indicated for the same condition, or may be used for the treatment of co-morbidities.

In particular embodiments, the compound of formula (I) may be selected from the group consisting of 1-(6,7-dihydro-5H-benzo[6,7]cyclohepta[1,2-c]pyridazin-3-yl)-$N^3$-(7-(pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-((7-(S)-pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-((7-(R)-pyrrolidin-1-yl)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-$N^3$-(3-fluoro-4-(4-(pyrrolidin-1-yl)piperidin-1-yl)phenyl)-1H-1,2,4-triazole-3,5-diamine;

1-(6,7-dihydro-5H-benzo[6,7]cyclohepta [1,2-c]pyridazin-3-yl)-$N^5$-(7-(pyrrolidin-1-yl)-6,7,8,9-tetrahydro-5H-benzo[7]annulene-1-yl)-1H-1,2,4-triazole-3,5-diamine;

1-(6,7-dihydro-5H-benzo[6,7]cyclohepta[1,2-c]pyridazin-3-yl)-$N^5$-(7-(S)-pyrrolidin-1-yl-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-((7S)-7-(t-butoxycarbonylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(acetamido)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-((2R)-2-(methoxycarbonyl)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4,4-difluoropiperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta [1,2-c]pyridazin-3-yl)-$N^3$-(7-((methoxycarbonylmethyl)(methyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-((2R)-2-(carboxy)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4-(ethoxycarbonyl)piperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4-(carboxy)piperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-((carboxymethyl)(methyl)

amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-(4-(ethoxycarbonylmethyl)piperazin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-(4-(carboxymethyl)piperazin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7-(pyrrolidin-1-yl)-6,7,8,9-tetrahydro-5H-benzo[7]annulene-1-yl)-1H-1,2,4-triazole-3,5-diamine;

1-(6,7-dihydro-5H-benzo[6,7]cyclohepta[1,2-c]pyridazin-3-yl)-N$^3$-((7S)-7-amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7s)-7-(di(cyclopropylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7S)-7((2-methylpropyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-((propyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(dipropylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(diethylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(cyclohexylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(cyclopentylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7S)-7-(1-cyclopentylethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(2-propylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7S)-7-(3,3-dimethylbut-2-yl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-((cyclohexylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(di(cyclohexylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7S)-7-(5-chlorothien-2-yl)methyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7S)-7((2-carboxyphenyl)methyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-(7S)-7-(3-bromophenyl)methyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(dimethylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(cyclobutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(3-pentylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7((2,2-dimethylpropyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(di(cyclopentylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-((cyclopentylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(di(bicyclo[2.2.1]hept-2-en-5-ylmethyl)amino)-6,7,8,9-tetrahydro-5H-benzo[7]annulene-2-y1)-1H-1,2,4-triazole-3,5-diamine;

1-(6,7-dihydro-5H-benzo[6,7]cyclohepta[1,2-c]pyridazin-3-yl)-N$^3$-((7S)-7-((bicyclo[2.2.1]hept-2-en-5-ylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(3-methylbutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(di(3-methylbutyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(2-ethylbutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(but-2-enylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(butyl(but-2-enyl)amino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]
pyridazin-3-yl)-$N^5$-(7S)-7-(t-butoxycarbonylamino)-6,
7,8,9-tetrahydro-5H-benzo[7]annulene-2-yl)-1H-1,2,4-
triazole-3,5-diamine;

1-(6,7-dihydro-5H-pyrido[2',3':6,7]cyclohepta[1,2-c]
pyridazin-3-yl)-$N^3$-((7S)-7-amino-6,7,8,9-tetrahydro-
5H-benzo[7]annulene-2-yl)-1H-1,2,4-triazole-3,5-di-
amine;

1-(6,7-dihydro-5H-pyrido[2',3': 6,7]cyclohepta[1,2-c]
pyridazin-3-yl)-$N^3$-((7S)-7-(dimethylamino)-6,7,8,9-
tetrahydro-5H-benzo[7]annulene-2-yl)-1H-1,2,4-triaz-
ole-3,5-diamine;

1-(6,7-dihydro-5H-pyrido[2',3': 6,7]cyclohepta[1,2-c]
pyridazin-3-yl)-$N^3$-((7S)-7-(diethylamino)-6,7,8,9-tet-
rahydro-5H-benzo[7]annulene-2-yl)-1H-1,2,4-triazole-
3,5-diamine;

1-(6,7-dihydro-5H-pyrido[2',3':6,7]cyclohepta[1,2-c]
pyridazin-3-yl)-$N^3$-((7S)-7-(dipropylamino)-6,7,8,9-
tetrahydro-5H-benzo[7]annulene-2-yl)-1H-1,2,4-triaz-
ole-3,5-diamine;

1-(6,7-dihydro-5H-pyrido[2',3':6,7]cyclohepta[1,2-c]
pyridazin-3-yl)-$N^3$-((7S)-7-(di(cyclopropylmethyl)
amino)-6,7,8,9-tetrahydro-5H-benzo[7]annulene-2-
yl)-1H-1,2,4-triazole-3,5-diamine;

1-(6,7-dihydro-5H-pyrido[2',3':6,7]cyclohepta[1,2-c]
pyridazin-3-yl)-$N^3$-((7S)-7-(di(3-methylbutyl)amino)-
6,7,8,9-tetrahydro-5H-benzo[7]annulene-2-yl)-1H-1,2,
4-triazole-3,5-diamine;

1-(6,7-dihydro-5H-pyrido[2',3':6,7]cyclohepta[1,2-c]
pyridazin-3-yl)-$N^3$-((7S)-7-(cyclobutylamino)-6,7,8,9-
tetrahydro-5H-benzo[7]annulene-2-yl)-1H-1,2,4-triaz-
ole-3,5-diamine;

1-(6,7-dihydro-5H-pyrido[2',3':6,7]cyclohepta[1,2-c]
pyridazin-3-yl)-$N^3$-((7S)-7-(cyclohexylamino)-6,7,8,
9-tetrahydro-5H-benzo[7]annulene-2-yl)-1H-1,2,4-tri-
azole-3,5-diamine;

1-(6,7-dihydro-5H-pyrido[2',3':6,7]cyclohepta[1,2-c]
pyridazin-3-yl)-$N^3$-((7S)-7-((methylethyl)amino)-6,7,
8,9-tetrahydro-5H-benzo[7]annulene-2-yl)-1H-1,2,4-
triazole-3,5-diamine;

1-(6,7-dihydro-5H-pyrido[2',3':6,7]cyclohepta[1,2-c]
pyridazin-3-yl)-$N^3$-((7S)-7-(cyclopentylamino)-6,7,8,
9-tetrahydro-5H-benzo[7]annulene-2-yl)-1H-1,2,4-tri-
azole-3,5-diamine; and 1-(6,7-dihydro-5H-pyrido[2',3':6,7]cyclohepta[1,2-c]
pyridazin-3-yl)-$N^3$-((7S)-7-(2-butylamino)-6,7,8,9-tet-
rahydro-5H-benzo[7]annulene-2-yl)-1H-1,2,4-triazole-
3,5-diamine The compound of formula (I) may, for example, be 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine In particular, the compound may be 1-(6,7-dihydro-5H-benzo[6,7]cyclohepta[1,2-c]pyridazine-3-yl)-$N^3$-(7-(S)-(pyrrolidin-1-yl)-6,7,8,9-tetrahydro-5H-benzo[7]annulene-2-yl)-1H-1,2,4-triazole-3,5-diamine.

In accordance with a second aspect of the present invention, there is provided a method for preventing, treating or managing a condition associated with the activation, mutation and/or over-expression of one or more kinases in a subject in need thereof, wherein if the condition is associated with Axl over-expression, it is also associated with the activation, mutation and/or over-expression of one or more other kinases, and wherein the method comprises administering to the subject a therapeutically or prophylactically effective amount of a compound that has a structure according to formula (I), as defined above.

All the embodiments mentioned above in connection with the first aspect of the invention are also applicable to the second aspect, as appropriate. Thus, the particular disease types, particular kinases, particular compounds etc. mentioned above are all applicable to the second aspect.

A third aspect of the present invention provides a method for reducing the activity of one or more kinases selected from those which are encoded by the genes MERTK (ENSG00000153208), TEK (ENSG00000120156), YES1 (ENSG00000176105), FLT1 (ENSG00000102755), FLT3 (ENSG00000122025), FLT4 (ENSG00000037280), BMX (ENSG00000102010), ABL1 (ENSG00000097007), RET (ENSG00000165731), KIT (ENSG00000157404), YSK4 (ENSG00000176601), SLK (ENSG00000065613), WEE1 (ENSG00000166483), WEE2 (ENSG00000214102), MAP3K2 (ENS G00000169967), MAP4K1 (ENS G00000104814), STK10 (ENSG00000072786), and LCK (ENSG00000182866), the method comprising contacting the kinase with an inhibitory amount of a compound that has a structure according to formula (I), as defined above.

In some embodiments of the third aspect, the method is carried out in vitro. In other embodiments, the method of the third aspect involves the administration, to a subject in need of such kinase activity reduction, of a therapeutically or prophylactically effective amount of a compound according to formula (I).

Also in accordance with the third aspect, there is provided a compound of formula (I), for use in reducing the activity of one or more of the kinases listed in connection with the third aspect.

The method of the third aspect allows for the in vitro or in vivo reduction in the activity of one or more of the listed kinases. In an in vivo setting, this may provide for symptomatic relief, prophylaxis or treatment of disease conditions where such conditions are associated (whether in a causative or consequential relationship) with activity of the kinase. In particular embodiments of the third aspect, the activity of the kinase is elevated compared to normal activity levels in an otherwise healthy population sample. The elevation of activity may, for example, be due to over-expression or mutation of the kinase.

In a fourth aspect, the present invention provides the use of a compound having a structure according to formula (I) as defined above, in the preparation of a medicament for treating, preventing or managing a condition associated with the activation, mutation and/or over-expression of one or more kinases, wherein if the condition is associated with Axl over-expression, it is also associated with the activation, mutation and/or over-expression of one or more other kinases.

In a fifth aspect, the present invention also provides a method of identifying a subject suitable for prophylaxis, management or treatment with a compound having a structure according to formula (I) as defined above, the method comprising determining the presence of the activation, mutation and/or over-expression of one or more kinases in a test subject, or in a biological sample obtained from a test subject, wherein the presence of said activation, mutation and/or over-expression of one or more kinases indicates the potential suitability of the subject for said prophylaxis, management or treatment, wherein if the test subject demonstrates Axl over-expression, the method also involves determining the presence of the activation, mutation and/or over-expression of one or more other kinases.

In an embodiment of the fifth aspect, the method includes a further step, after the determination step, of administering to the subject a compound having a structure according to formula (I) as defined above, for the purposes of the prophylaxis, management or treatment of a condition associated with the activation, mutation and/or over-expression of one or more kinases.

Where the method of the fifth aspect employs a biological sample obtained from a test subject, the sample may comprise blood, tissue (e.g. a tissue biopsy), tumour cells (e.g. a tumour biopsy), bone marrow, sputum, saliva or faeces.

Suitable techniques for determining the activation, mutation and/or over-expression of one or more kinases in a test subject, or in a biological sample obtained from a test subject, will be known to the skilled person. For determining expression levels, such techniques include polymerase chain reaction (PCR)-based methods (such as quantitative PCR), fluorescent in situ hybridisation, transcription level (i.e. mRNA) sequencing methods. For determining mutant status, the following approaches are exemplary: PCR-based amplification and sequencing (for example using mutation specific primers), PCR and single-strand conformation polymorphism, whole genome (in particular, tumour genome) sequencing, multiplex high-throughput gene mutation analysis, melting curve analysis.

In more detail, selection of subjects susceptible to treatment with a compound of formula (I) as defined herein can be determined by evaluating the kinase mutant status and expression levels using suitable methods. There are numerous methods to study kinase mutant status and expression levels, and the list of steps below is intended to present examples only: (i) isolating a sample from formalin-fixed, paraffin-embedded specimens or fresh, frozen, or alcohol-fixed sections of a cell, group of cells, an animal model or human; (ii) determining the expression level of kinases of interest (eg. those listed in Table 4) by a testing method with sufficient performance characteristics Such methods for determining expression level can include transcript level analysis by quantitative Polymerase Chain Reaction (qPCR) (Arne G, et al., Int J Cancer, September 1; 129(5):1149-61 (2011); Ouerhani S, Cancer Genet. September; 205(9):436-41 (2012)), Immunohistochemistry (IHC) (Zhang H, et al. J Cancer Res Clin Oncol. February; 135(2):249-53. (2009)), Fluorescent in situ hybridization (FISH) diagnosis (Fløisand et al., Scand Clin Lab Invest. 68(2):93-8 (2008)) or transcription level sequencing, methods; (iii) determining the mutant status of kinases (for example, those listed in Table 4) by a testing method with sufficient performance characteristics. Such methods for determining mutant status can include PCR based amplification and sequencing (Guo J J, et al. J Clin Oncol, August 10; 29(23):e672-4 (2011); Ouerhani S, Cancer Genet. September; 205(9):436-41 (2012); Sritana N, Exp Mol Pathol, December; 85(3):227-31. (2008); Bains A, et al., Am J Clin Pathol. January; 135(1):62-9. (2011)), PCR and single-strand conformational polymorphism (SSCP) (ss secondary structure analysis) (Stirewatt DL, et al., Nat Rev Cancer, September; 3(9):650-65.(2003)2.), Tumor genome sequencing (Love C, et al,, Nat Genet. December; 44(12):1321-5. (2012); Kanagal-Shamanna R et al., Mod Pathoi. August 2. (2013)), Multiplex high-throughput gene mutation analysis (Dunlap J, et aL, Hum Pathol. December; 43(12):2167-76 (2012)), melting curve analysis (Poláková K M, et al., Leuk Res, August; 32(8):1236-43 (2008)).

As a specific example, to study Ber-Abl mutation status, first obtain blood or bone marrow samples from subjects. Isolate RNA using TriReagent (Sigma-Aldrich) and perform cDNA synthesis using MMIN reverse transcriptase (Promega). Perform polyinera.se chain reaction (PCR) using the following primers: (5'-GAAGCTTCTCCCTGACATCCGT-3') and (5'-GCCAG GCTCTCGGGTGCAGTCC-3'). Following electrophoresis. excise the resulting 1.3 kb fragment from a low melting point agarose gel. Perform a standard Sanger sequencing on the gel-purified 1.3 kb fragment specific to the Abl kinase domain using the primers (5'-GCGCAACAAGCCCACTGTCT-3') and (5'-GCCAG-GCTCTCGGGTGCAGTCC-3') and analyze T315I mutation and homotheterozygotes by peak-heights.

The particular kinases, kinase mutants, particular compounds, particular disease types etc. mentioned above in connection with the first aspect are all applicable to the third, fourth and fifth aspects.

Figure 2:
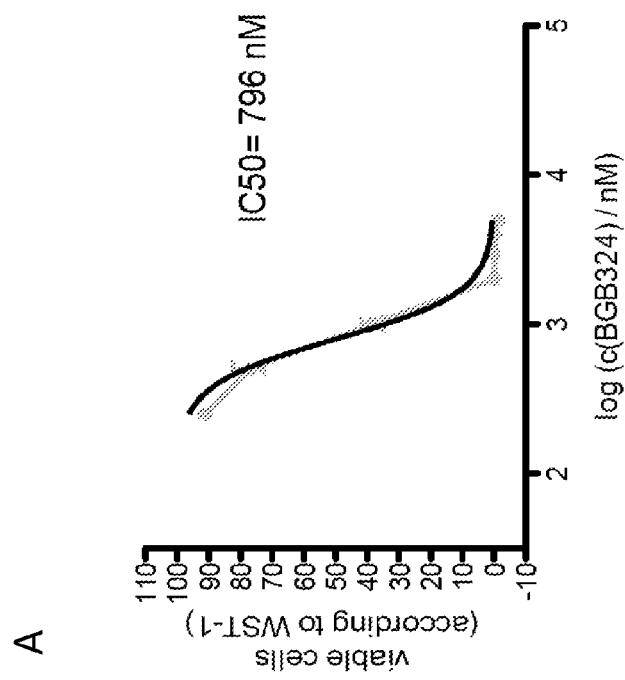
Figure 2:
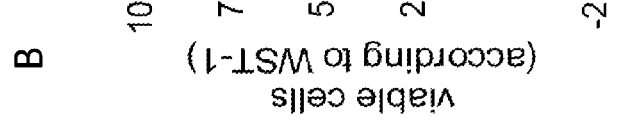
Figure 3:
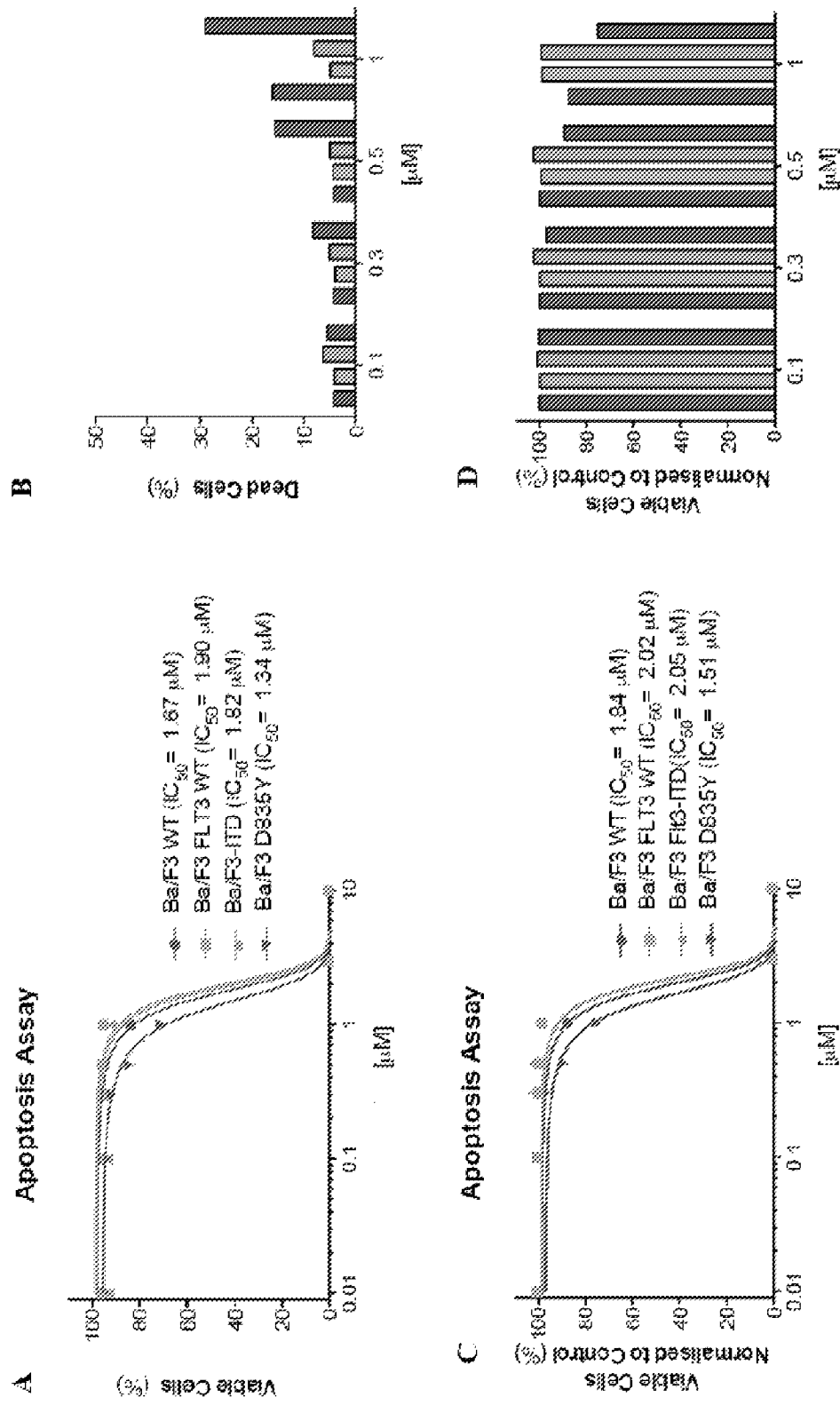
Figure 4:
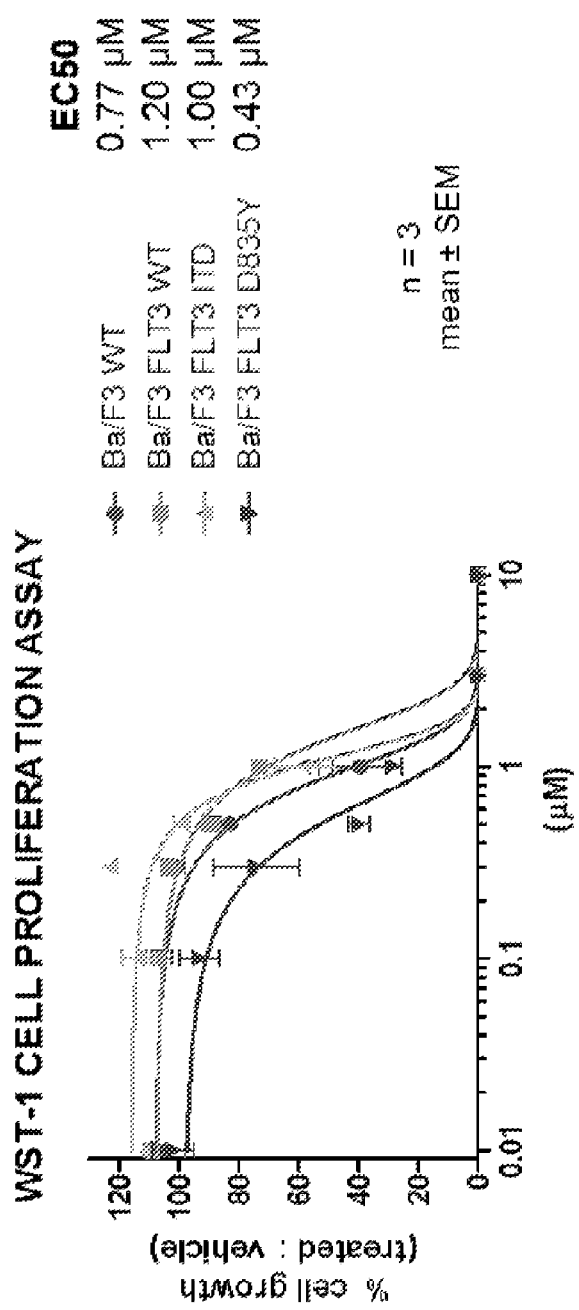
Figure 4:
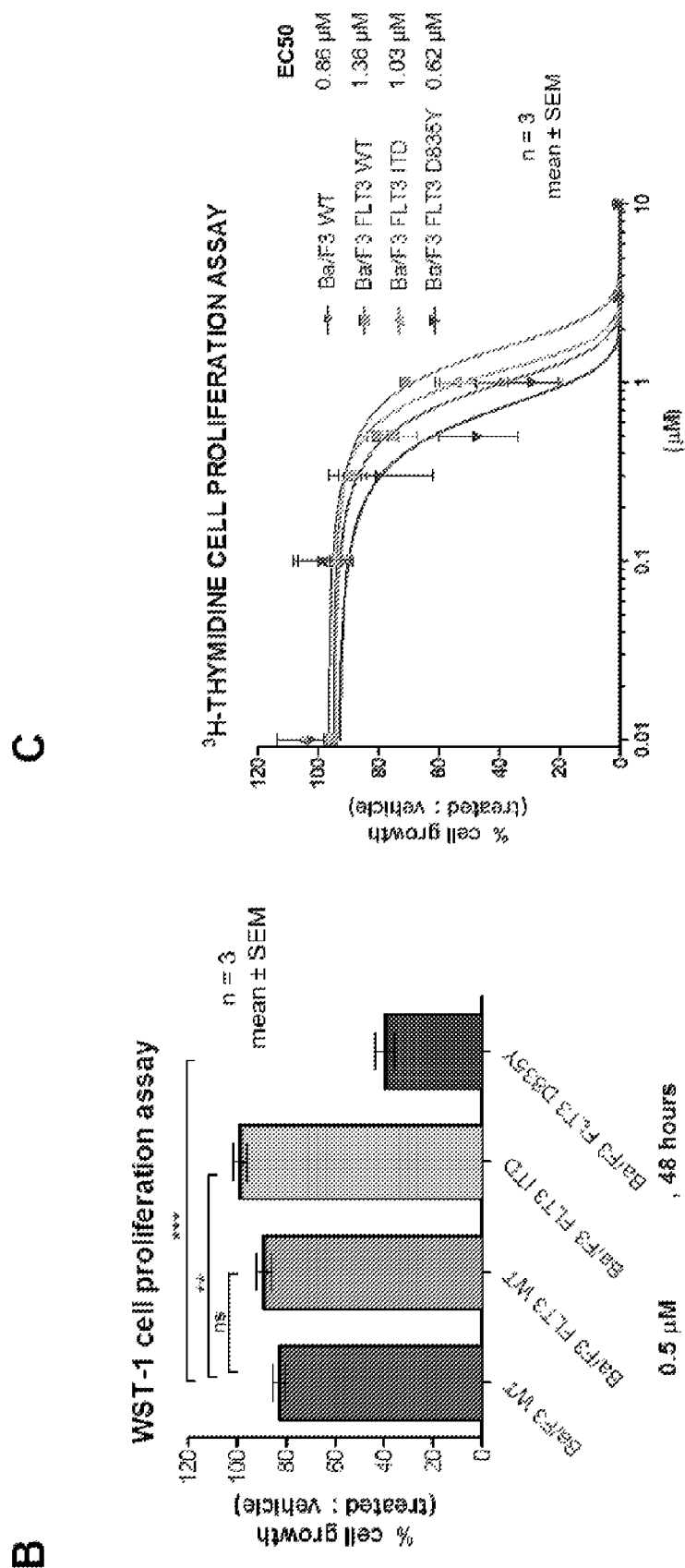
Figure 5:
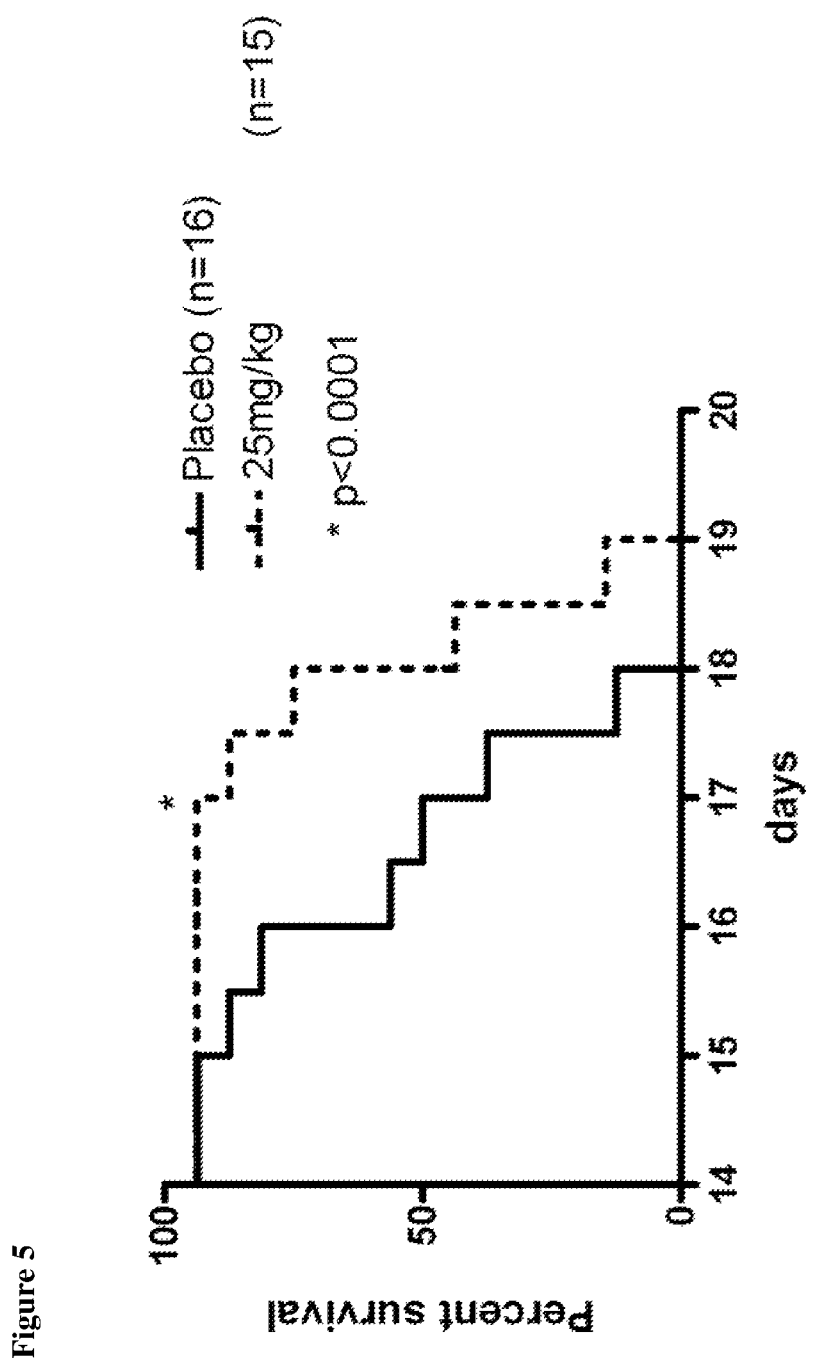
Figure 6:
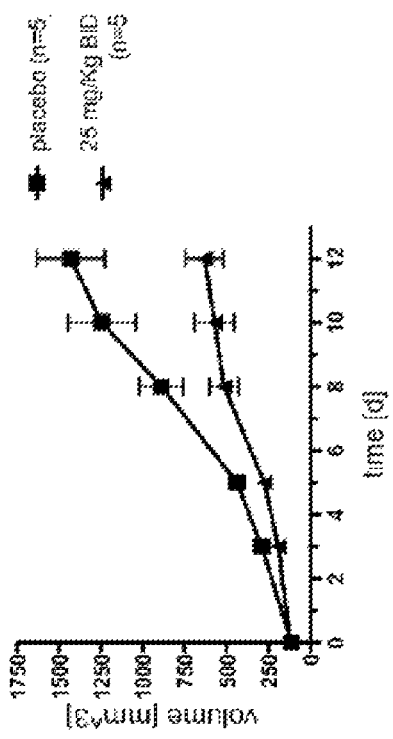
Figure 6:
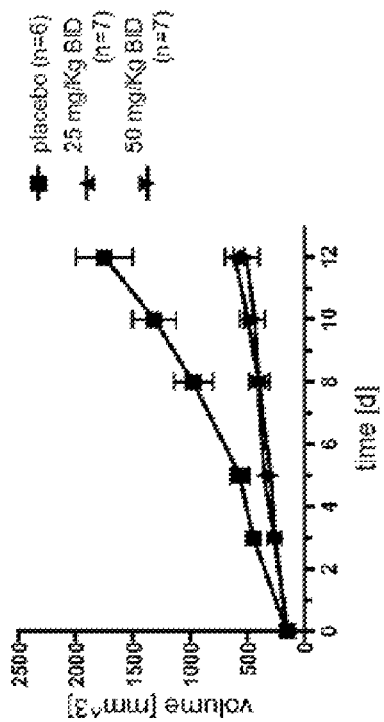

The invention will now be described in more detail by way of example only, with reference to the appended figures:

FIG. 1, which shows A) $K_d$ determination KinomeScan study 2 (0.4 nM); and B) $IC_{50}$ determination KinaseProfiler Study 5 (5 nM);

FIG. 2, which shows the results of cell viability tests conducted with Compound A in Ba/F3 cells expressing Bcr-Abl1 in its non-mutated form (A) or expressing the T315I mutant (B);

FIG. 3 shows viability of four Ba/F3 cell lines differing in expression of none, wild type or mutated FLT3 following compound A treatment. Cells were treated with compound A (0, 0.01, 0.1, 0.3, 0.5, 1, 3 and 10 µM) for 48 hours and the cell viability was measured by flow cytometry employing annexin V and PI as apoptotic markers as described above (gating of flow cytometric data not shown). (A) Percent viability plotted as a dose response curve from raw data obtained in the double negative gate for Annexin V and PI. IC50 values included. (B) Bar charts represent raw data of dead cells, treated with 0.1, 0.3, 0.5, 1 µM compound A for 48 hours. Dead cells include both early and late apoptotic cells, and likewise necrotic cells. (C) Percent viability plotted as a dose response curve from to control normalized data obtained in th double negative gate for Annexin V and PI. Controls were set to 100%. IC50 values included. (D) Bar charts represent normalized data of viable cells, treated with 0.1, 0.3, 0.5, 1 µM compound A for 48 hours. In (B) and (D), the results are presented from left to right, at each concentration, for the cell types in the same order as the listing of cell types in (A) and (C). In each instance, concentration of compound A is displayed on the x-axis;

FIG. 4. Proliferation of wild-type (WT), FLT3 wild-type, FLT3 ITD and FLT3 D835Y Ba/F3 cells following compound A treatment. (A) Proliferation of cells after treatment with 0.01, 0.1, 0.3, 0.5, 1, 3, 10 µM compound A for 48 hours, with WST-1 added to assess oxidoreductase activity at the last 4 hours. Results were compared with untreated controls and presented as the mean±SEM of three independent experiments. The EC50 value of each cell clone was indicated at the right side of figure (B) WST-1 cell proliferation assay of cells after treatment with 0.5 µM compound A for 48 hours. Results were compared with untreated controls and displayed as the mean±SEM of three separate experiments (ns: not significant, : p<0.01, *: p<0.001). (C) $^3$H-Thymidine (i.e. tritiated thymidine) incorporation cell proliferation assay of cells after treatment with 0.01, 0.1, 0.3, 0.5, 1, 3, 10 µM compound A for 48 hours, with $^3$H-Thymidine added at the last 18 hours. Results were compared with untreated controls and presented as the mean±SEM of three different experiments. The EC50 value of each cell line is indicated at the right side of the image. Concentrations on the x-axes refer to compound A;

FIG. 5 shows that compound A reduced leukemia cell burden in an aggressive preclinical CML model in which bone marrow cells were retrovirally transduced with constructs containing T315I-mutated BCR-ABL1. Doses refer to compound A; and FIG. 6 shows that compound A potentially inhibits T315I mutated and wild type CML in vivo. Doses refer to compound A.

EXAMPLES

Example 1

1-(6,7-dihydro-5H-benzo[6,7]cyclohepta[1,2-c]pyridazine-3-yl)-N³-(7-(S)-(pyrrolidin-1-yl)-6,7,8,9-tetrahydro-5H-benzo[7]annulene-2-yl)-1H-1,2,4-triazole-3,5-diamine (hereinafter 'compound A') is a potent and selective inhibitor of Axl kinase with a Kd of 0.4 nM (KinomeScan™ method) and an $IC_{50}$ of 5-15 nM for the inhibition of kinase activity in the absence of serum protein (KinaseProfiler™ and cell-based assays).

At 4 to 10-fold higher concentrations, there is potential for binding/inhibition of other non-mutant kinases (e.g. Ysk4, MerTK, Stk10, TEK, Wee1, and Yes).

Compound A also bound and inhibited a number of mutant kinases including the "gatekeeper" mutation in chronic myeloid leukemia, Abl1(T315I), cKit(D816H), Flt3 (D835Y), Ret(V804L and M) and TEK (Y897S and R849W) at 1 to 10-fold higher concentrations compared with Axl, suggesting that several mutant kinases may provide alternative targets for this compound. Abl(T315I) is frequently found upon development of resistance to the Abl kinase inhibitor imatinib in CML, while cKit(D816H) is often found following development of resistance to imatinib and sunitinib in GIST.

Although the Examples contained herein demonstrate the ability of Compound A to inhibit multiple kinases beyond Axl, these results should also be considered to demonstrate the inhibitory activity of other compounds of formula (I). As shown in WO2008/083367, a wide variety of compounds of formula (I) have similar binding and activity at Axl, and it is therefore expected that such a congeneric series of compounds would have similar applicability to that demonstrated herein for Compound A in the inhibition of other kinases.

Background

Compound A is an orally bioavailable Axl kinase inhibitor suitable for example for the treatment of cancer. The compound has shown single agent activity as well as activity in combination with other anticancer agents in limiting primary tumor and metastatic tumor growth.

The kinase selectivity of Compound A has important safety and efficacy implications with regard to on- and off-target activities. Secondary kinase activities could potentially contribute to additional anti-tumour activity.

These Examples report the kinase selectivity data from studies conducted by EMD Millipore Corp. (Billerica, Mass., USA) and DiscoveRx Corporation (San Diego, Calif., USA) using different biochemical assay methodologies. The different studies are listed in Table 1 below:

TABLE 1

| Study no. | Provider | Methods | Notes |
|---|---|---|---|
| 1 | EMD Millipore | KinaseProfiler ™ | Panel of 128 kinases |
| 2 | DiscoveRx | KinomeScan ™ | Largest available panel – 451 wildtype and mutant kinases |
| 3 | EMD Millipore | KinaseProfiler ™ | Confirmation of mutant kinase results from study 2 in second assay |
| 4 | EMD Millipore | KinaseProfiler ™ | Confirmation of key results from studies 1, 2 and 3 |

Note that these assays measure the effect of Compound A in different ways and under different conditions (e.g. ATP concentration, serum concentration). As a result the values obtained can vary from assay to assay. This is particularly prominent where the assay includes serum: Compound A binds tightly to plasma protein (>99%) in animals and humans, which will affect the effective free concentration of drug in these assays. In contrast to the KinaseProfiler assays, which measure the effect of Compound A on kinase activity, the KinomeScan assay estimates the binding constant $K_d$ between Compound A and the kinase.

Materials and Methods

Detailed assay methodologies can be found in the relevant references cited herein, or in the KinaseProfiler Service Assay Protocols (v54, 2011) available from EMD Millipore (www.emdmillipore.com), or from the KinomeScan website (www.kinomescan.com), as appropriate. (For a more detailed description of KINOMEscan's assay technology, see: Fabian et al. A small molecule-kinase interaction map for clinical kinase inhibitors. Nat. Biotechnol. 23, 329-336 (2005)). A summary is provided below.

KinaseProfiler™ assays (EMD Millipore Corp. Billerica, Mass., USA) are radioligand binding assays with purified or partially-purified human kinases. Most of the KinaseProfiler™ assays are conducted in 20 mM MOPS, 1 mM EDTA, 0.01% Brij-35, 5% Glycerol, 0.1% b-mercaptoethanol, 1 mg/mL BSA. The assay involves the transfer of $^{32}$P from γ-$^{32}$P-ATP to the target peptide, followed by washing and trapping of the labeled peptide on a filter. The concentration of γ-$^{32}$P-ATP used was at the established $K_m$ for ATP. Specific assay protocols for individual kinases can be found using the www.emdmillipore.com reference mentioned above.

KinomeScan™ assays (DiscoveRx Corporation, San Diego, Calif., USA) are active-site-directed competition binding assays. Briefly, Compound A binding to the kinase active site can directly (sterically) or indirectly (allosterically) prevent kinase binding to an immobilized ligand, reducing the amount of a DNA-labeled kinase captured on a solid support. Test molecules that do not bind the kinase have no effect on the amount of kinase captured on the solid support. The amount of kinase captured in test versus control samples is determined by using a qPCR method that detects the associated DNA label on each kinase molecule. Dissociation constants ($K_d$) for test compound-kinase interactions are calculated by measuring the amount of kinase captured on the solid support as a function of the test compound concentration. An 11-point $K_d$ determination was performed for Axl (0.005 nM to 300 nM) followed by 5-point (0.4, 4, 40, 400, 4000 nM) determinations for the entire 451-kinase panel. GraphPad Prism was used to estimate an IC50 based on these data.

Results

Potency Against Axl Kinase

An 11-point $K_d$ determination in study 2 suggests a $K_d$ of 0.4 nM (FIG. 1A) in the KinomeScan assay. The value estimated from the 5-point determination used in the full survey of 451 kinases is in reasonably good agreement at 0.7 nM.

In the three KinaseProfiler-based studies (1, 3 and 4) the $IC_{50}$ was 4.6±1.5 nM (FIG. 1B), in the presence of 90 µM ATP (the established Km for ATP for Axl kinase). Holland et. al. Cancer Res. 70: 1544-54 (2010) reported an $IC_{50}$ value of 14 nM for compound A at Axl.

Potency Against Other Wild-Type Kinases

Table 2 below compares the results obtained in the different studies summarized here. Listed in the table are a variety of wild-type kinases that clearly responded to Compound A with an average $IC_{50}$ or $K_d$ within 10-fold of the response of Axl kinase in at least one of the biochemical assays. Where the same kinase was tested multiple times in the same assay, the average is shown. Tyro3 kinase is included in the table because it is a member of the TAM family of receptor tyrosine kinases—the kinases (Tyro3, Axl, MerTK) that are most closely related to Axl. Also shown is the fold-difference between the value obtained for the kinase and the average value obtained for Axl in the same assay.

TABLE 2

Inhibition of wildtype kinases by Compound A.
Biochemical assays

| Kinase | KinomeScan | | KinaseProfiler | |
|---|---|---|---|---|
|  | nM | Fold | nM | fold |
| Axl | 0.4 | 1 | 4.6 | 1 |
| Ysk4 | 1.6 | 4 | n/a | |
| MerTK | 100 | 250 | 12.5 | 2.7 |
| Stk10 | 9.2 | 23 | 22 | 4.7 |
| TEK | 270 | 680 | 30 | 6.4 |
| Wee1 | 17 | 42 | 32 | 6.9 |
| Ret | 73 | 180 | 38 | 8.1 |
| Flt1 | 400 | >1000 | 40 | 8.7 |
| Flt4 | 460 | >1000 | 41 | 8.8 |
| Yes | 810 | >1000 | 43 | 9.2 |
| Tyro3 | >1000 | >1000 | 413 | 89 |

(n/a = Kinase not available in this assay format)

In binding assays (KinomeScan) Compound A bound strongly to Axl and Ysk4. However, in kinase-activity based biochemical assays (KinaseProfiler) eight additional kinases showed inhibition with $IC_{50}$<10× the $IC_{50}$ to Axl.

Potency Against Mutant Kinases

The KinomeScan study no. 2 included a number of mutant kinases found in human tumours, some of which are known to be driver mutations of cancer growth. Several of these showed unexpectedly higher Compound A binding than their wild-type versions. Where available these and related mutant kinases were therefore also tested in the KinaseProfiler assay (study 3) to obtain confirmation in a second assay system. The results are summarized in Table 3.

TABLE 3

Inhibition of mutant kinases by Compound A compared to inhibition of wild-type kinase

| Kinase | Biochemical assays | | | |
|---|---|---|---|---|
|  | KinomeScan | | KinaseProfiler | |
|  | nM | fold | nM | fold |
| Axl | 0.4 | 1 | 4.6 | 1 |
| Abl | 52 | 130 | 51 | 11 |

TABLE 3-continued

Inhibition of mutant kinases by Compound A compared to inhibition of wild-type kinase

| Kinase | Biochemical assays | | | |
|---|---|---|---|---|
|  | KinomeScan | | KinaseProfiler | |
|  | nM | fold | nM | fold |
| Abl(Q252H) | 112 | 280 | 16 | 3.5 |
| Abl(Y253F) | 18 | 45 | 26 | 5.6 |
| Abl (T315I) | 10 | 25 | 4 | 0.9 |
| Abl(M351T) | 104 | 260 | 32 | 7.0 |
| Abl(H396P) | 57 | 140 | 22 | 4.8 |
| c-Kit | 104 | 260 | 1284 | 279 |
| c-Kit (V560G) | n/a | | 45 | 9 |
| c-Kit (V654A) | n/a | | 286 | 62 |
| c-Kit (D816H) | 63 | 160 | 8 | 1.7 |
| c-Kit (D816V) | 10.2 | 26 | 177 | 38 |
| Flt3 | 50 | 125 | 122 | 26 |
| Flt3 (D835H) | 8.4 | 21 | n/a | |
| Flt3 (D835Y) | 11.2 | 28 | 13 | 2.8 |
| Ret | 73 | 180 | 22 | 4.8 |
| Ret (M918T) | 30 | 75 | n/a | |
| Ret (V804L) | 90 | 225 | 11 | 2.4 |
| Ret (V804M) | 72 | 180 | 21 | 4.6 |
| TEK | 270 | 675 | 41 | 8.9 |
| TEK(Y897S) |  |  | 13 | 2.8 |
| TEK(R849W) |  |  | 22 | 4.8 |

Compound A in this assay was shown to be a potent inhibitor of several mutant kinases. In particular, Compound A inhibits Abl(T315I), the gatekeeper mutation of Abl kinase, with a potency similar to its inhibition of Axl itself. Several other Abl kinase mutations are inhibited within a 10-fold range of Axl as well. The cKit mutant c-Kit(D816H) is also inhibited within the same concentration range as Axl. c-Kit(D816H) mutations have been detected in patients with GastroIntestinal Stromal Tumours (GIST) who develop acquired resistance to imatinib and sunitinib therapy (Gajiwala et. al. Proc. Natl. Acad. Sci. 106:1542-7 (2009)).

Discussion

In addition to inhibiting Axl, Compound A also showed significant activity against several other kinases. In several cases Compound A showed significant activity against cancer-associated mutant kinases but not against the unmutated kinases.

Based on competition binding assays that measure the degree of binding of Axl to the kinase active-site ATP-binding pocket (KinomeScan™), Compound A shows strong binding to Axl ($K_d$=0.4 nM) and Ysk4 ($K_d$=1.6 nM). Ysk4 is a member of the STE kinase family.

KinaseProfiler™ assays of kinase inhibition conducted on over 130 kinases identified at least nine with potential to be inhibited by Compound A with $IC_{50}$<46 nM (10 times the Axl $IC_{50}$ of 4.6 nM): Axl, MerTK, Stk10 (LOK), TEK, Wee1, Ret, Flt1, Flt4, Yes.

The combined evidence thus suggests that in addition to inhibiting Axl, Compound A may potentially also inhibit at least Ysk4, MerTK, Stk10, TEK, Wee1, Ret, Flt1, Flt4 and Yes kinases at concentrations 4 to 10-fold above those required for Axl inhibition.

In addition to these wild-type kinases, there is evidence that Compound A inhibits some mutant kinases much more potently than their wild-type parents. Most significant of these is the potent inhibition of Abl(T315I) ($IC_{50}$=4 nM). The Abl(T315I) mutation is known as the "gatekeeper" mutation for its role in the escape of chronic myeloid leukemia from treatment with imatinib Similarly, potent inhibition was seen against Kit(D816H), a mutation that arises with acquired resistance to imatinib and sunitinib in patients with Gastrointestinal Stromal Tumours (GIST). Other mutations of Abl kinase that arise during development of resistance were also inhibited in a range of 16-32 nM Compound A. The Flt3 mutations D835H, D835Y, K663Q, and A829P were all inhibited in the range of 8-29 nM. Compound A activity against cancer-associated mutated kinases but not the unmutated kinases is less likely to cause unwanted side-effects as normal tissues should be unaffected. These activities suggest possible applications of Compound A against these mutant kinases.

A summary of associations between mutant kinases and disease conditions is provided in Table 4 below by way of example.

TABLE 4

Known mutant kinases and their related diseases

| Gene mutation | Cancer Type | Reference |
|---|---|---|
| ABL1 | Chronic myeloid leukemia (CML), Acute lymphoblastic leukaemia (ALL), multiple myeloma (MM) | 1. Shah NP, et al., Cancer Cell. August; 2(2):117-25 (2002) 2. Langabeer SE, et al., Acta Haematol. 126(4):214-5 (2011) 3. Breitkopl SB, et al. Proc Natl Acad Sci USA. October 2; 109(40):16190-5 (2012) |
| KIT | Gastrointestinal stromal tumors (GIST), melanoma, CML, acute myeloid leukemia (AML), clear cell renal cell carcinoma (KIT overexpression) | 1. Arne G, et al., Int J Cancer. September 1; 129(5):1149-61 (2011) 2. Guo JJ, et al. J Clin Oncol. August 10; 29(23):e672-4 (2011) 3. Ouerhani S, Cancer Genet. September; 205(9):436-41 (2012) 4. Sritana N, Exp Mol Pathol. December; 85(3):227-31. (2008) 5. Zhang H, et al. J Cancer Res Clin Oncol. February; 135(2):249-53. (2009) |
| FLT3 | Myelodysplastic syndromes (MDS), AML | 1. Stirewalt DL, et al., Nat Rev Cancer. September; 3(9):650-65.(2003)2. 2. Bains A, et al., Am J Clin Pathol. January; 135(1):62-9. (2011) |
| RET | Medullary thyroid carcinoma, Non-small cell lung carcinoma, lymphoma, Pheochromocytoma, | 1. Figlioli G, et al., Mutat Res. January-March; 752(1):36-44. (2013) 2. Yokota K, et al., Oncol Rep. October; 28(4):1187-92. (2012) 3. Love C, et al., Nat Genet. December; 44(12):1321-5. (2012) 4. Sjursen W, et al., Fam Cancer. September; 12(3):529-35. (2013) |

Selectivity of Compound A for Cells Expressing Mutant Kinases

FIG. 2 shows that Ba/F3 bone marrow derived mouse cells expressing T315I mutated Bcr-Atl1 fusion protein are more sensitive to Compound A (IB50 570 nM) compared to cells expressing the non-mutated Bcr-Abl1 kinase (IC50 796 nM).

Ba/F3 cells either stably overexpressing Bcr-Abl1 (A) or the mutant Bcr-Abl1 T315I (B) were cultured overnight in serum free RPMI-1640 media supplemented with 2 mM glutamine, 100 U/mL penicillin and 100 µg/mL streptomycin (Sigma-Aldrich). The following day, cells were plated in a 96-well plate with each well containing 2000 cells in a volume of 100 µl serum free RMPI media. Subsequently, 50 µl of serum free RPMI media containing different concentrations of Compound A were added (triplicates). Final Compound A concentrations in each well were 0, 250, 500, 1000, 2000, 3000, 4000 and 5000 nM. The 96 well plates were incubated for 48 hours, and cell viability was measured in a WST-1 assay (Roche). Briefly, 5 µl WST-1 solution was added to each well and the 96-well plate was incubated for another 2 hours. The readout was performed in an ELSA reader at 480 nm. (measure)/620 nm (reference). Subsequent data analysis was performed with Microsoft Excel 2003 and GraphPad Prism 4.0.

The results confirm that a compound of formula (I) shows greater cytotoxicity against cells expressing a. mutant kinase, compared to equivalent cells not bearing the mutation.

Conclusions

Compound A is a potent inhibitor of Axl kinase with a Kd of 0.4 nM and an $IC_{50}$ of 5-15 nM for the inhibition of kinase activity in the absence of serum protein. Binding to/inhibition of other non-mutant kinases (for example, Ysk4, MerTK, Stk10, TEK, Wee1, and Yes) may occur in the range of 4 to 10-fold higher concentrations. Compound A also bound and inhibited a number of mutant kinases including the "gatekeeper" mutation in chronic myeloid leukemia, Abl(T315I), cKit(D816H), Flt3(D835Y), Ret(V804L and M) and TEK(Y897S and R849W) at less than 10-fold higher concentrations compared with Axl inhibition, suggesting that several mutant kinases may provide alternative targets for this compound and related compounds of formula (I). Abl(T315I) is frequently found upon development of resistance to the Abl kinase inhibitor imatinib in CML, while cKit(D816H) is often found following development of resistance to imatinib and sunitinib in GIST.

Example 2

In Vitro Evaluation of Compound A in FLT3 Mutated Ba/F3 Cells

Objective

The aim of this study was to perform an evaluation of a novel, highly selective small molecule inhibitor of the Axl receptor tyrosine kinase compound A in the treatment of acute myeloid leukemia (AML). We wished to assess compound A efficacy by evaluating the cell viability of four different Ba/F3 cell lines (wild-type Ba/F3 cells or Ba/F3 cells expressing either wild-type or mutated FLT3) following exposure to compound A. Compound A was added to Ba/F3 cells in eight concentrations (0, 0.01, 0.1, 0.3, 0.5, 1, 3, 10 µM) and incubated for 48 hours. Treated Ba/F3 cells were assayed for proliferation (WST-1 and 3H-Thymidine incorporation) and for detection of apoptotic markers annexin V and propidium iodide (PI), allowing the determination of EC50 and IC 50 values.

Materials and Methods

Cell lines

Murine pro-B lymphocyte line Ba/F3 wild type (Ba/F3 WT), and Ba/F3 lines stably transduced with expression vectors that encoded wild-type human FLT3 (Ba/F3 FLT3 WT cells) or human FLT3 containing an ITD mutation (Ba/F3-ITD cells) or D835Y (Ba/F3 D835Y cells) point mutations, which lead to constitutively functional activation of the protein, were obtained from Bjørn Tore Gjertsen (Department of Clinical Science, Hematology Section, University of Bergen, Bergen, Norway). Ba/F3 WT, Ba/F3 FLT3 WT and Ba/F3 835Y cells were maintained in RPMI-1640 medium, containing 10% fetal calf serum (FCS, HyClone, Logan, UT), 2 mM L-glutamine and 50 U/mL penicillin-streptomycin (Sigma-Aldrich, Inc, St Louis, Mo., USA), and 10% WEHI-3B conditioned medium as a source of murine interleukin-3 (mIL-3). Ba/F3-ITD cells were maintained in the absence of mIL-3

Compounds

Compound A was dissolved in DMSO and stored at −20° C. When used in cell culture work, the final concentration of DMSO did not exceed 0.05%.

Apoptosis Detection and Cell Proliferation Assays

Ba/F3 cells were incubated overnight before and during treatment period in the medium containing 0.1 ng/mL of mIL-3 (Prospec BIO, USA).

Apoptosis/Cell Death Assay

Quantification of apoptotic and necrotic cells was determined by measuring externalization of phosphatidylserine with annexin V, conjugated to Alexa® Fluor 647 (Invitrogen, Molecular Probes, OR, USA) and using propidium iodide (PI; Sigma-Aldrich) as a dead-cell counterstain. To assess cell viability of Ba/F3 cells (WT, FLT3 WT, FLT3-ITD, D835Y) in vitro, cells were seeded at the density of $1 \times 10^5$ cells per ml of medium on 24-well plates, and then treated with compound A (0, 0.01, 0.1, 0.3, 0.5, 1, 3, 10 μM) for 48 hours. After drug treatment cells were stained according the manufacturer's protocol, and subsequently analysed on an Accuri C6 flow cytometer (Becton Dickinson Immunocytometry Systems, San Jose, Calif., USA). FlowJo software version 10 (Tree Star, Inc., Ashland, Oreg., USA) was used for data analysis. Both, early apoptotic (Annexin V-positive, PI-negative), late apoptotic (Annexin V-positive and PI-positive) and necrotic cells (Annexin V-negative and PI-positive) were included in cell death determinations. The percent viable cells are expressed as percentage of untreated cells, performed in a single experiment. IC50 values were determined as the EC50 of the inhibitor; the concentration that provokes a response half way between the maximal (FIG. 3A Top) response and the maximally inhibited (FIG. 3A Bottom) response.

WST-1 Cell Proliferation Assay

Proliferation of cells was assessed using the tetrazolium salt WST-1 that is cleaved to chromogenic formazan dye by mitochondrial dehydrogenases in viable cells. Ba/F3 cells were seeded in triplicate at a density of $10 \times 10^3$ cells in 100 μL of medium per well on 96-well plates, treated with compound A (0, 0.01, 0.1, 0.3, 0.5, 1, 3, 10 μM) for 48 hours, and WST-1 (Roche Ltd, Basel, Switzerland) was added into each well with the dilution 1:11 at the last 4 hours of treatment period. The absorbance of the samples was measured by Spectramax Plus 384 Spectrophotometer (Molecular Devices Corp., Sunnyvale, Calif., USA) and the percentage of proliferation was calculated by using the following formula:

(Arbitrary units (AU) of treated sample–AU of background control)/(AU of untreated sample–AU of background control).

$^3$H-Thymidine Incorporation Cell Proliferation Assay

Ba/F3 cells were seeded in triplicate at a density of $10 \times 10^3$ cells in 100 μL of medium per well on 96-well plates, treated with compound A (0, 0.01, 0.1, 0.3, 0.5, 1, 3, 10 μM) for 30 hours, and addition of $^3$H-Thymidine (1 μCi/well; TRA310, Amersham International, Amersham, UK). Following 18 hours incubation, the DNA was harvested and radioactivity was assessed by liquid scintillation counting (Packard Microplate Scintillation and Luminescence counter, Perkin Elmer Life and Analytical Science, Inc., Waltham, USA).

Statistical Analysis

Statistical analyses were performed using Prism Version 5.0 software (GraphPad Software, La Jolla, Calif.). Results for proliferation assays are presented as means±SEM. Data were compared using an unpaired, 2-tailed Student t-test. Differences greater than P=0.05 were considered significant.

Results:

Apoptosis Detection and Cell Proliferation Assays

Viability following compound A treatment (0, 0.01, 0.1, 0.3, 0.5, 1, 3 and 10 μM) after 48 hours was assessed for four clones of Ba/F3 cell lines, using the Annexin V-PI assay. Dose-response curves (FIGS. 3A and 3C) indicated a narrow therapeutic window of compound A (0.5-3 μM) in the investigated Ba/F3 cell lines. Treatment with 1 μM compound A for 48 hours showed the greatest difference in efficacy between cell lines (FIGS. 3B and 3D). The mutated Ba/F3 D835Y cell line appeared to be most sensitive to compound A treatment (FIG. 3).

A massive induction of apoptosis was observed for all cell lines regardless of FLT3 status, when incubated with higher doses of Axl inhibitor (≥3 μM). Viable and dead cells were gated from a population of interest without any debris and containing only single cells. Viable cells were characterized with double negativity for both apoptotic markers, while dead cells contained early apoptotic (annexin V+/PI−), late apoptotic (annexin V+/PI+) and necrotic cells (annexin V−/PI+).

WST-1 and $^3$H-Thymidine Incorporation Cell Proliferation Assays

The results of cell proliferation assays indicate that the Ba/F3 cells are very responsive in a very narrow concentration range of compound A. By 3 μM of compound A, all cells are dead regardless of cell line. Nonetheless, it can be seen that the Ba/F3 FLT3 D835Y cell line is the most sensitive. The Ba/F3 FLT3 ITD demonstrates comparable sensitivity to Ba/F3 WT and BaF3 FLT3 WT (FIG. 4).

Conclusion

In this study, we demonstrated that a highly selective small molecule inhibitor of the Axl receptor tyrosine kinase compound A has a narrow therapeutic window (0.5-3 μM) in investigated clones of Ba/F3 cell lines. Both apoptotic and proliferation assays gave comparable results and confirmed that Ba/F3 D835Y cell line is the most sensitive to Axl inhibition by compound A treatment.

Example 3

FIG. 5 shows that compound A reduced leukemia cell burden in an aggressive preclinical CML model in which bone marrow cells were retrovirally transduced with constructs containing T315I-mutated BCR-ABL1.

Methods:

6- to 8 week old male Balb/c mice were sublethally irradiated and i.v. injected with $0.5 \times 10^6$ retroviral transduced BM cells (pMSCV_gfp/BCR-ABL_T315I). After 3 days mice were randomized and treated twice per day with compound A (25 (or 50) mg/Kg mice) or placebo.

Bone marrow donor mice: To harvest donor bone marrow mice were injected subcutaneously with 5-FU (150 mg/kg mice). The bone marrow was isolated five days later and transduced with the desired retroviral construct. [Daley, G. Q., R. A. Van Etten, and D. Baltimore, Induction of chronic myelogenous leukemia in mice by the P210bcr/abl gene of the Philadelphia chromosome. Science, 1990. 247(4944): p. 824-30.]

Example 4

FIG. 6 shows that compound A potentially inhibits T315I mutated and wild type CML in vivo.

Methods:

6- to 8-week-old male NSG mice were implanted subcutaneously with $1 \times 10^7$ BaF3/wt-BCR-ABL or $1 \times 10^7$ BaF3/T315I cells per mouse into the right flank. Five days after implantation mice were randomized into groups with a mean volume of approximately 100 mm$^3$. Animals were treated twice per day (via gavage) with compound A (25 (or 50) mg/kg mice) or placebo. Tumor volume was measured every 2-3 days. Animals were sacrificed at day 12 and tumors embedded for histology.

The invention claimed is:

1. A method for reducing the activity of one or more mutant kinases selected from those which are encoded by the genes ABL 1(T315I), ABL 1(Q252H), ABL1(H396P), ABL1(Y253F), ABL1(M351T), ABL1(E255K), KIT (A829P), KIT(D816H), KIT(V560G), KIT(D816V), KIT (V654A), FLT3(D835Y), FLT3(D835H), FLT3(K663Q), FLT3(N841I), RET(V804L), RET(V804M), RET(M918T), TEK(Y897S), and TEK(R849W), the method comprising contacting the kinase with an inhibitory amount of a compound selected from the group consisting of:

1-(6,7-dihydro-5H-benzo[6,7]cyclohepta[1,2-c]pyridazin-3-yl)-N3-(7-(pyrrolidin-1-yl)-6,7,8,9-tetrahydro-5H-benzo[7]annulene-2-yl)-1H-1,2,4-triazole-3,5-diamine; and 1-(6,7-dihydro-5H-benzo[6,7]cyclohepta[1,2-c]pyridazin-3-yl)-N3-((7-(S)-pyrrolidin-1-yl)-6,7,8,9-tetrahydro-5H-benzo[7]annulene-2-yl)-1H-1,2,4-triazole-3,5-diamine.

2. A method according to claim 1, wherein the method is carried out in vitro.

3. A method according to claim 1, wherein the method involves the administration, to a subject in need of such kinase activity reduction, of a therapeutically or prophylactically effective amount of the compound.

4. The method according to claim 1, wherein the compound is used in sequential or simultaneous combination with one or more additional active pharmaceutical ingredients.

5. The method according to claim 1, wherein the compound is 1-(6,7-dihydro-5H-benzo[6,7]cyclohepta[1,2-c]pyridazine-3-yl)-$N^3$-(7-(pyrrolidin-1-yl)-6,7,8,9-tetrahydro-5H-benzo[7]annulene-2-yl)-1H-1,2,4-triazole-3,5-diamine.

6. The method according to claim 5, wherein the compound is 1-(6,7-dihydro-5H-benzo[6,7]cyclohepta[1,2-c]pyridazine-3-yl)-$N^3$-(7-(S)-(pyrrolidin-1-yl)-6,7,8,9-tetrahydro-5H-benzo[7]annulene-2-yl)-1H-1,2,4-triazole-3,5-diamine.

7. The method according to claim 1, wherein the method is for the provision of symptomatic relief, prophylaxis or treatment of fibrosis.

8. The method according to claim 7, wherein the fibrosis is liver fibrosis.

* * * * *